United States Patent [19]

Gahwyler

[11] 4,110,438
[45] Aug. 29, 1978

[54] METHOD OF TREATING DEPRESSION

[75] Inventor: Max Gahwyler, Darien, Conn.

[73] Assignee: American Home Products Corporation, New York, N.Y.

[21] Appl. No.: 779,373

[22] Filed: Mar. 21, 1977

[51] Int. Cl.$^2$ .................. A61K 37/00; C07C 103/52
[52] U.S. Cl. ........................ 424/177; 260/112.5 LH
[58] Field of Search .............. 424/177; 260/112.5 LH

[56] References Cited

PUBLICATIONS

G. Bissette, et al., Pharm. Biochem. and Behavior 5, pp. 135–138, 1976.
R. Ehrensing, et al., Pharm. Biochem. and Behavior 5, pp. 89–93, 1976.
Lifton, Pharmaocl. Biochem. Behavior 5, 135–138 (1976).
Kastin, Pharmaocl. Biochem. Behavior 5, 89–93, (1976).
O. Benkert, et al., The Lancet (1974), p. 1146.
L. P. Renaud, et al., Nature 255, (1975), pp. 233–235.

Primary Examiner—Delbert R. Phillips

[57] ABSTRACT

A method of treating depression using luteinizing hormone-releasing hormone is disclosed.

5 Claims, No Drawings

METHOD OF TREATING DEPRESSION

BACKGROUND OF THE INVENTION (a) Field of the Invention

This invention relates to a method of treating depression with luteinizing hormone-releasing hormone.

(b) Prior Art

The most extensively used method for treating moderate to severe depression involves the administration of tricyclic antidepressant agents. Examples of such agents are amitriptyline, nortriptyline, imipramine, desipramine and doxepin. These drugs, however, have several disadvantages. Among the serious disadvantages are a delayed onset of effectiveness of one to two weeks, and side effects such as atropine-like side effects, e.g., dry mouth, tachycardia, etc., and central nervous system side effects, e.g., parkinsonism, drowsiness, etc.

Consequently, efforts have recently been made to develop an improved method for treating depression. For example, see N. P. Plotalkoff, U.S. Pat. No. 3,737,549, issued June 5, 1973 relating to the treatment of depression with thyrotropin releasing agent. However, none of these recent efforts have replaced or supplemented the above mentioned method.

Thus, there is a need for an improved method of treating depression, especially one which would have a rapid onset of effectiveness and would be free of the above mentioned side effects of the tricyclic antidepressants. The present invention provides such a method.

SUMMARY OF THE INVENTION

According to the present invention, an improved method of treating a patient suffering from depression is disclosed, comprising:

administering to said patient a therapeutically effective amount of luteinizing hormone-releasing hormone, or a therapeutically acceptable acid addition salt thereof.

DETAILED DISCRIPTION OF THE INVENTION

The effective agent for the present method is "luteinizing hormone-releasing hormone", hereinafter referred to as LH-RH. A. V. Schally et al, Biochem. Biophys. Res. Commun., 43, 393 and 1334(1971), isolated this hormone from pig hypothalami and proposed the decapeptide structure (pyro)-Glu-His-Trp-Ser-Tyr-Gly-Leu-Arg-Pro-Gly-NH$_2$. This structure of LH-RH has been confirmed by synthesis; for example, see H. Matsuo et al., Biochem. Biophys. Res. Comm., 45, 822(1971). An extremely practical synthesis for producing this hormone in a high degree of purity has been reported by H. Immer et al., J. Med. Chem., 17, 1060(1974); see also U.S. Pat. No. 3,835,108, issued September 10, 1974 to Immer et al.

LH-RH now has become a useful therapeutic and diagnostic agent. It is used for treating endocrinological disorder such as disturbances of the cycle, amenorrhea, lack of development of secondary sex characteristics, female infertility, delayed puberty and cryptorchidism. As a diagnostic tool, it is useful for distinguishing between hypothalamic and pituitary malfunction in the human female.

Now it has been found that when 100-800 mcg of LH-RH, or a therapeutically acceptable acid addition salt thereof, is administered to a moderately to severely depressed patient, symptoms of depression disappear usually within 24 hours and the patient becomes cheerful and aware of feeling much better. Usually effective results are obtained by administering 200-500 mcg of LH-RH. The dose is administered in a single or divided dose on a monthly basis and can be repeated, if required, usually on a monthly basis.

Depressions have often been classified on the basis of etiology, e.g. reactive if produced by environmental stresses and endogenous if no precipitating factor can be demonstrated and the depression is thought to arise 'from within', perhaps on a genetic basis, see M. Sim and E. B. Gordon in "Basic Psychiatry", E. & S. Levingstone Ltd., Edinburgh and London, 1968, p. 139.

Especially effective and favorable results are obtained when LH-RH in the dosages noted above are administered to patients suffering from stress induced depression, i.e., reactive depression. Stress induced depression includes, for example, depression that is sometimes experienced by over-worked executives or people who have experienced a family death. The stress induced depression frequently is associated with suicidal tendencies, as well as impotency in males or loss of libido in females.

The above findings are indeed surprising in view of an earlier report that the administration to patients with endogenous depression of LH-RH, thyrotropin releasing hormone and a placebo in randomized order on days 1, 3 and 5 was of no clinical importance in the treatment of endogenous depression, see O. Benkert et al, Lancet, ii, 1146(1974).

Example of preferred therapeutically acceptable salts are those of the pharmaceutically acceptable acids, e.g. hydrochloric acid, acetic acid, lactic acid succinic acid, panoic acid and the like. See U.S. Pat. No. 3,835,108, cited above, for other examples of therapeutically acceptable salts.

For application according to the method of this invention, LH-RH can be formulated into various pharmaceutical dosage forms as disclosed in U.S. Pat. No. 3,835,108, cited above. In a preferred mode of administration the LH-RH is given parenterally with a pharmaceutically acceptable liquid or solid carrier. A particularly useful formulation comprises LH-RH, or a therapeutically acceptable salt, in a sterile aqueous solution which may also contain other solutes such as buffers and preservatives, as well as sufficient pharmaceutically acceptable salts or glucose to make the solution isotonic. The dosage will vary with the form of administration and is preferably kept at a level of from 1.0 mcg to 20 mcg per kilogram of body weight per month. However, a dosage level in the range of from about 1.0 mcg to about 10 mcg per kilogram of body weight per month is most desirably employed in order to achieve effective results.

The effectiveness of LH-RH, to treat a patient suffering from depression is demonstrated by the following clinical investigation.

Twenty-one patients, suffering from depression caused by stress or emotional exhaustion, were selected for the investigation. Fifteen were female adults, five were male adults and one patient was a young male under twelve years of age. The latter patient suffered from existential depression and cryptorchidism. Each patient received 300 mcg of LH-RH in a single or divided dose once a month. In this instance the LH-RH was in the form of its hydrochloride acid addition salt and was prepared according to the syntheses reported by Immer et al., noted above.

Following the administration of the LH-RH, response was immediate. Relief from depression usually was observed within 12 hours and in almost all cases within 24 hours. The patients became more cheerful and aware of feeling much better. Sleep and appetite were regularized as well as disposition for work. An improvement in libido response occurred frequently and was most noticeable in the female patients. Only one patient did not respond. This latter patient sufferred from depression and sexual frigidity; however, in this instance there was no anhedonia regression and some erotic pulsations did occur.

In the younger patients there was a gonadotropin response; growth of the penis and development of the scrota were measured and photographically documented at 30 and 60 days after the beginning of treatment.

During treatment, hormonal responses to LH-RH, i.e. increases in the serum levels of luteinizing hormone, follicular stimulating hormone, prolactin and thryrotrophin releasing hormone, were monitered. The greatest hormonal responses coincided with the most evident clinical improvement.

In a control study, five patients with established depression were treated with an injection of only the vehicle for the above noted LH-RH dosage. No clinical improvement or changes in hormonal indices were observed with these patients.

I claim:

1. A method of treating a patient suffering from stress induced depression comprising administering to said patient a therapeutically effective amount of luteinizing hormone-releasing hormone, or a therapeutically acceptable salt thereof.

2. The method of claim 1 wherein the amount of luteinizing hormone-releasing factor is from 100 to 800 mcg.

3. The method of claim 1 wherein the amount of luteinizing hormone-releasing factor is from 200 to 500 mcg.

4. The method of claim 1 wherein the therapeutically acceptable acid addition salt is the hydrochloric acid addition salt.

5. The method of claim 1 wherein the luteinizing hormone-releasing hormone, or a therapeutically acceptable salt, is administered parenterally in an amount from 1.0 mcg to 20 mcg per kilogram of body weight per month.

* * * * *